(12) United States Patent
Harwin et al.

(10) Patent No.: US 6,458,135 B1
(45) Date of Patent: Oct. 1, 2002

(54) FEMORAL GUIDE FOR IMPLANTING A FEMORAL KNEE PROSTHESIS AND METHOD

(75) Inventors: Steven F. Harwin, New York, NY (US); Stuart L. Axelson, Succasunna; David J. Neal, Oak Ridge, both of NJ (US)

(73) Assignee: Howmedica Osteonics Corp., Allendale, NJ (US)

( * ) Notice: Subject to any disclaimer, the term of this patent is extended or adjusted under 35 U.S.C. 154(b) by 0 days.

(21) Appl. No.: 09/776,240

(22) Filed: Feb. 2, 2001

(51) Int. Cl.⁷ .............................................. A61B 17/90

(52) U.S. Cl. ...................................................... 606/88

(58) Field of Search ............................ 606/79, 80, 82, 606/87, 88, 89, 96, 102

(56) References Cited

U.S. PATENT DOCUMENTS

| | | | |
|---|---|---|---|
| 5,486,178 A | | 1/1996 | Hodge |
| 5,624,444 A | * | 4/1997 | Wixon et al. .................. 606/88 |
| 5,662,656 A | * | 9/1997 | White .......................... 606/88 |
| 5,810,831 A | | 9/1998 | D'Antonio |
| 5,860,980 A | * | 1/1999 | Axelson, Jr. et al. ......... 606/88 |
| 6,013,081 A | * | 1/2000 | Burkinshaw et al. ......... 606/88 |
| 6,033,410 A | * | 3/2000 | McLean et al. ............... 606/88 |
| 6,056,756 A | * | 5/2000 | Eng et al. ..................... 606/87 |
| 6,096,043 A | | 8/2000 | Techiera et al. |

OTHER PUBLICATIONS

Olcott et al, "A Comparison of 4 Intraoperative Methods to Determine Femoral Component Rotation during Total Knee Arthroplasty," *The Journal of Arthroplasty*, vol. 15, No. 5, Sep./Oct., 1996, 1058–1062.

Johnson & Johnson Orthopaedics, "P.F.C. Sigman Knee System," undated.

"The Fudger—The Ultimate Weapon in the Femoral Referencing War," Orthopaedic Update, *Number 18, undated.*

Biomet Inc., "Simple Instruments: Surgical Technique for the Knee," 10–11.

* cited by examiner

*Primary Examiner*—Eduardo C. Robert
(74) *Attorney, Agent, or Firm*—Arthur Jacob (57) ABSTRACT

A femoral guide is shown in the form of a femoral sizing guide for determining the size of a femoral knee prosthesis to be implanted at an implant site at a distal femur and includes a femoral sizing block connected to a foot component for selective pivotal movement about a pivotal axis extending in a generally axial direction and essentially intersecting the transepicondylar axis of the distal femur to enable a guide arrangement on the femoral sizing block to be located for facilitating subsequent placement of a femoral cutting guide on a distal femur in position to rotationally locate an anterior cut in a plane anterior of and essentially parallel to the transepicondylar axis of the distal femur. The femoral sizing block is connected to the foot component for selective linear movement to compensate for size variations outside standard femoral knee prosthesis sizes. Visible indications are provided of the location of a subsequently implanted femoral knee prosthesis. A corresponding method determines the appropriate location and position of the femoral knee prosthesis to be implanted at the implant site, and the size of the femoral knee prosthesis.

26 Claims, 4 Drawing Sheets

FEMORAL GUIDE FOR IMPLANTING A FEMORAL KNEE PROSTHESIS AND METHOD

BACKGROUND OF THE INVENTION

1. Field of the Invention

The present invention relates generally to the implant of prosthetic joints and pertains, more specifically, to the preparation of the distal femur for the implant of a femoral knee prosthesis, utilizing a femoral guide, such as a femoral sizing guide for the subsequent location of a femoral cutting guide, to assist in establishing the surfaces necessary for locating and securing the prosthesis in place on the femur.

2. Description of the Related Art

The implant of a prosthetic knee joint requires that the distal femur be prepared to receive the femoral component of the knee prosthesis by cutting the bone of the femur to establish accurately located surfaces against which the femoral knee prosthesis will rest upon implant of the femoral component. Various guides are available to the surgeon for assisting in guiding a saw blade during use of the saw blade to make the femoral cuts which establish the desired surfaces. These guides usually are located and secured on the distal femur, often upon a transverse surface established initially at the distal femur, to provide guide surfaces for guiding the saw blade during the execution of an axially directed anterior femoral cut, an axially directed posterior femoral cut, an anterior chamfer and a posterior chamfer, all specifically related to the size of the femoral knee prosthesis to be implanted and to the position and orientation of the femoral knee prosthesis at the site of the implant. The appropriate location of a femoral cutting guide, then, generally requires the use of a femoral sizing guide to determine the size of the femoral knee prosthesis which will be implanted at an implant site in a particular recipient, and to locate the corresponding femoral cutting guide appropriately on the transverse distal femoral surface for proper placement of the femoral knee prosthesis upon implant at the implant site.

Femoral knee prostheses are made available in a range of standard sizes. A femoral sizing guide is used to assist in the selection of a standard size femoral knee prosthesis which will best fit the requirements of a particular implant site. Once selected, the femoral knee prosthesis must be located and oriented so as to attain appropriate rotational alignment and create a symmetric flexion gap. Various intraoperative methods have been employed to determine femoral component rotation during knee arthroplasty. Among these methods are: (1) the use of the Whiteside line (line connecting the intercondylar notch and the patellar groove) as a reference; (2) the use of the transepicondylar axis (line connecting the high points of the epicondyles) as a reference; (3) the use of the posterior condylar axis (three degrees of external rotation off the posterior femoral condyles) as a reference; and (4) determining the femoral component necessary to form a symmetric flexion gap after ligament balance is complete in one or both of flexion and extension. It has been demonstrated that the use of the transepicondylar axis to determine femoral component rotation is, in most instances, the most reliable method for achieving the desired femoral component rotation.

SUMMARY OF THE INVENTION

The present invention provides a femoral guide and method and, in particular, a femoral sizing guide and method which facilitates the selection and orientation of a femoral knee prosthesis of appropriate standard size at a given implant site. As such, the present invention attains several objects and advantages, some of which are summarized as follows: Provides a single instrument for assisting a surgeon in the interoperative selection of a femoral knee prosthesis of standard size, and fitting the selected component for optimum position and orientation utilizing as a reference the demonstrated reliability of the transepicondylar axis; enables the surgeon to select and fit a femoral knee component of standard size at an implant site where the indicated size requirement does not coincide directly with a standard size, while still attaining optimum positioning and orientation of the implanted femoral knee prosthesis; enables an accurate and stable preparation for the appropriate size femoral knee prosthesis when the sizing procedure initially indicates a size which falls in-between standard available sizes; provides increased accuracy and stability in the location of a femoral guide at the distal femur; lessens the risk of creating an undesirable preparation at the distal femur; provides the surgeon with an advantageous technique for increasing the accuracy of the sizing procedure and concomitant accurate location of an appropriate femoral cutting guide, with added ease and lessened time; minimizes the need for guessing or for visual estimation in determining proper sizing and proper positioning of a femoral cutting guide, and especially proper rotational positioning, during femoral preparations for the implant of a femoral knee prosthesis; permits the surgeon to create a predictable and accurate femoral resection for exemplary performance in the completed implanted knee prosthesis.

The above objects and advantages, as well as further objects and advantages, are attained by the present invention which may be described briefly as a femoral guide for use in connection with the implant of a femoral knee prosthesis at an implant site at a distal femur of a femur extending in an axial direction within a recipient, the distal femur having a transepicondylar axis extending transverse to the axial direction, the femoral guide being arranged for engagement with the distal femur to enable interoperative determination of an optimum location and orientation of at least one femoral cut appropriate to accommodate the knee prosthesis at the implant site, the femoral guide comprising: a femoral block for engagement with the distal femur, the femoral block having a guide arrangement for determining the location and orientation of the at least one femoral cut; a support component for placement at a predetermined position relative to the distal femur; and a pivotal connection connecting the support component with the femoral block for pivotal movement of the femoral block relative to the support component about a pivotal axis extending generally in the axial direction and essentially intersecting the transepicondylar axis so as to enable orientation of the femoral block to rotationally position the guide arrangement for subsequent rotational orientation of the at least one femoral cut relative to the transepicondylar axis.

In addition, the present invention includes a femoral sizing guide for use in selecting a femoral knee prosthesis of a standard size for implant at an implant site at a distal femur of a femur extending in an axial direction within a recipient, the distal femur having posterior condyles with corresponding posterior condylar surfaces, a prepared distal femoral surface, and a transepicondylar axis extending transverse to the axial direction, the femoral sizing guide being arranged for engagement with the prepared distal femoral surface and the posterior condylar surfaces to provide a size indication for a femoral knee prosthesis of a size appropriate for the implant site, and enabling interoperative determination of an optimum location and orientation of an anterior cut appropriate to accommodate the selected knee prosthesis of standard size at the implant site, the femoral sizing guide comprising: a femoral sizing block having a block locator surface for extending transverse to the axial direction upon engagement of the femoral sizing block with the prepared distal surface, and a guide arrangement for determining the location of a femoral cutting guide to be placed subsequently at the distal femur for guiding execution of the anterior cut; a foot component including foot locator surfaces projecting in the axial direction for engaging the posterior condylar surfaces upon engagement of the block locator surface with the prepared distal femoral surface; and a pivotal connection connecting the foot component with the femoral sizing block for pivotal movement of the femoral sizing block relative to the foot locator surfaces to enable orientation of the femoral sizing block to locate the guide arrangement for subsequent placement of the femoral cutting guide in position to locate the anterior cut in a plane anterior of and essentially parallel to the transepicondylar axis.

Further, the present invention provides a method of utilizing a femoral guide in connection with implanting a femoral knee prosthesis at an implant site at a distal femur of a femur extending in an axial direction within a recipient, the distal femur having a transepicondylar axis extending transverse to the axial direction, the femoral guide being arranged for engagement with the distal femur to enable interoperative determination of an optimum location and orientation of at least one femoral cut appropriate to accommodate the knee prosthesis at the implant site, the method comprising: engaging a femoral block of the femoral guide with the distal femur, the femoral block further having a guide arrangement for determining the location and orientation of the at least one femoral cut; placing a support component at a predetermined position relative to the distal femur; and pivotally moving the femoral block relative to the support component about a pivotal axis extending generally in the axial direction and essentially intersecting the transepicondylar axis so as to enable orientation of the femoral block to rotationally position the guide arrangement for subsequent rotational orientation of the at least one femoral cut relative to the transepicondylar axis.

Still further, the present invention includes a method of utilizing a femoral sizing guide for implanting a selected femoral knee prosthesis of a standard size at an implant site at a distal femur of a femur extending in an axial direction within a recipient, the distal femur having posterior condyles with corresponding posterior condylar surfaces, a prepared distal femoral surface, and a transepicondylar axis extending transverse to the axial direction, the femoral sizing guide being arranged for engagement with the prepared distal femoral surface and the posterior condylar surfaces to provide a size indication for a femoral knee prosthesis of a size appropriate for the implant site, and enabling interoperative determination of an optimum location and orientation of an anterior cut appropriate to accommodate the selected knee prosthesis of standard size at the implant site, the method comprising: engaging a femoral sizing block of the femoral sizing guide with the prepared distal surface, the femoral sizing block having a block locator surface such that the block locator surface rests against the prepared distal surface and extends transverse to the axial direction, the femoral sizing block further having a guide arrangement for determining the location of a femoral cutting guide to be placed subsequently at the distal femur for guiding execution of the anterior cut; engaging a foot component with the posterior condylar surfaces upon engagement of the block locator surface with the prepared distal femoral surface, the foot component including foot locator surfaces projecting in the axial direction for engaging the posterior condylar surfaces; and pivotally moving the femoral sizing block relative to the foot locator surfaces to enable orientation of the femoral sizing block to locate the guide arrangement for subsequent placement of the femoral cutting guide in position to locate the anterior cut in a plane anterior of and essentially parallel to the transepicondylar axis.

BRIEF DESCRIPTION OF THE DRAWING

The invention will be understood more fully, while still further objects and advantages will become apparent, in the following detailed description of preferred embodiments of the invention illustrated in the accompanying drawing, in which.

DESCRIPTION OF THE PREFERRED EMBODIMENTS

Figure 1:
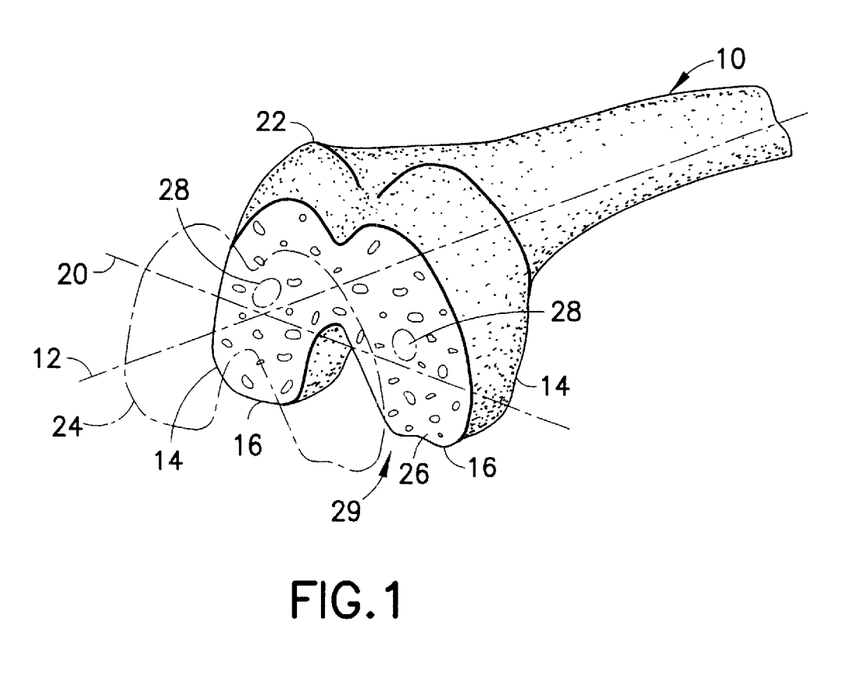
FIG. 1 is a pictorial perspective view of a distal femur, prepared with a transverse distal femoral surface.

Referring now to the drawing, and especially to FIG. 1 thereof, a femur is illustrated at 10 and is seen to extend in an axial direction, along longitudinal axis 12, and includes condyles 14 having posterior condylar surfaces 16, and a transepicondylar axis 20. Femur 10 has a distal end 22 which has undergone initial preparation for the implant of a femoral component of a knee prosthesis (not shown) to the extent that a distal portion (shown in phantom at 24) has been removed and a distal surface 26 has been established at the distal end 22. Distal surface 26 extends transverse to the axial direction, and the transverse distal surface 26 is planar. A pair of axially extending holes 28 are to be drilled into the bone of the femur 10 for the reception and location of a femoral cutting guide (not shown) which will be used to complete the preparation of the distal femur at implant site 29, as explained in greater detail in U.S. Pat. Nos. 4,892,093 and 5,810,831.

Figure 2:
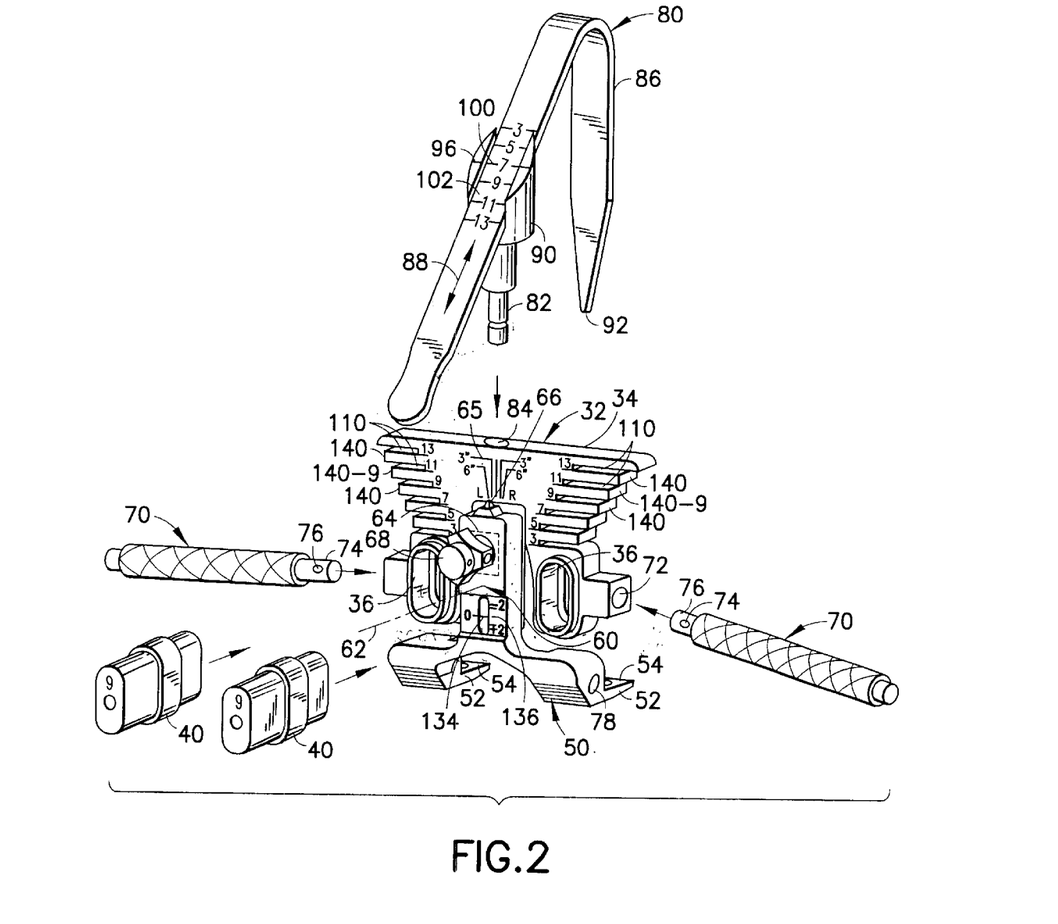
FIG. 2 is an exploded pictorial perspective view, enlarged over FIG. 1, showing a femoral sizing guide constructed in accordance with the present invention.
Figure 3:
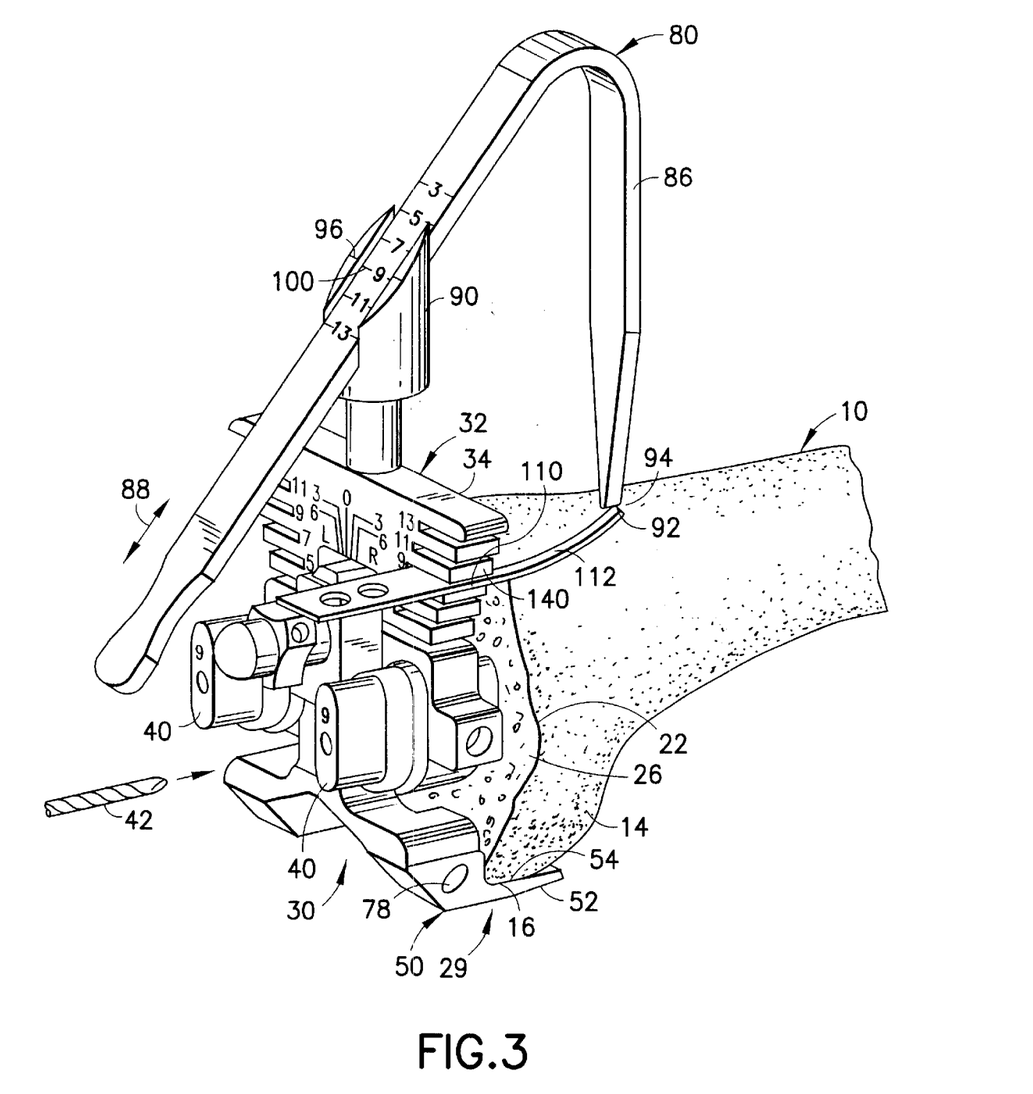
FIG. 3 is a pictorial perspective view of the femoral sizing guide placed at the distal femur.

Turning now to FIG. 2, in order to determine the size of the femoral knee prosthesis and place the holes 28 for the reception of a femoral cutting guide of corresponding size in appropriate location and orientation relative to the distal femur, a femoral guide constructed in accordance with the invention is illustrated in the form of a femoral sizing guide 30 for placement against the distal end 22 of femur 10. Femoral sizing guide 30 includes a femoral block in the form of femoral sizing block 32 having a planar block locator surface 34 which is to be seated upon the transverse distal surface 26, as shown in FIG. 3. A guide arrangement on the femoral sizing guide 30 includes guide elements in the form of openings 36 adapted to receive drill guides 40 for guiding a drill 42, upon proper location of the femoral sizing guide 30 upon the distal femur, to place holes 28 so as to determine the precise location of the femoral cutting guide to be placed subsequently at the distal femur for guiding of the femoral cuts necessary to complete the preparation of the distal femur for the reception of the femoral knee prosthesis.

A support component in the form of foot component 50 includes support elements comprising a pair of laterally spaced-apart locating feet 52 which project in axial directions, essentially normal to the planar block locator surface 34, and to the transverse distal surface 26. Each locator foot 52 includes a foot locator surface 54. Upon proper seating of the femoral sizing guide 30 at the distal end 22 of the femur 10, planar block locator surface 34 is placed against transverse distal surface 26 and the feet 52 are placed against the condyles 14 of the distal femur, with the foot locator surfaces 54 engaging respective posterior condylar surfaces 16 to place the foot component 50 at a prescribed position relative to the distal femur.

A pivotal connection at 60 connects the foot component 50 with the femoral sizing block 32 for pivotal movement of the femoral sizing block 32 relative to the foot component 50 and, consequently, relative to feet 52 and the foot locator surfaces 54. Pivotal movement of the femoral sizing block 32 is about pivotal axis 62 which extends generally in an axial direction, essentially normal to the block locator surface 34, and which essentially intersects the transepicondylar axis 20. Upon proper seating of the femoral sizing guide 30, with the foot locator surfaces 54 engaging the respective posterior condylar surfaces 16 to place the foot component 50 at the prescribed position relative to the distal femur, as described above, pivotal positioning of the femoral sizing block 32, relative to the foot component 50, enables orientation of the femoral sizing block 32 to locate and rotationally position the openings 36 for subsequent placement of the femoral cutting guide 30 to locate and orient the femoral cuts relative to the transepicondylar axis 20.

More particularly, as seen in FIG. 2, pivotal movement of the femoral sizing block 32 relative to the foot component 50 enables orientation of the anterior plane associated with a subsequent anterior cut so that the anterior plane will be essentially parallel to the transepicondylar axis 20. In the illustrated preferred embodiment, the pivotal connection 60 includes an incremental arrangement in the form of a detent mechanism, shown diagrammatically at 64, for allowing selective pivotal movement of the femoral sizing block 32 relative to the foot component 50 in predetermined fixed increments of angular displacement, illustrated at scale 65 as 3° and 6° left rotation, and 3° and 6° right rotation, relative to a neutral, or zero, position. A pointer 66 indicates the selected rotation, and a locking knob 68 secures the selected rotation. The predetermined fixed increments of angular displacement are chosen to match the most common values of angular rotation encountered in recipients. The rotation ordinarily is pre-set prior to placing the femoral sizing guide 30 at the implant site 29; however, should interoperative adjustments become necessary, based upon observations by the surgeon during the implant procedure, manipulating handles 70 are available for quick connection to the femoral sizing block 32, thereby facilitating accurate alignment of the anterior plane essentially parallel with the transepicondylar axis 20 at the implant site 29. To this end, femoral sizing block 32 includes laterally opposite sockets 72, manipulating handles 70 include complementary plugs 74 for reception within sockets 72, and a quick-disconnect mechanism in the form of a ball detent arrangement 76 secures each plug 74 within a corresponding socket 72. A further securement hole 78 is provided adjacent each foot 52 for the reception of supplemental securement pins (not shown) which can be directed through holes 78 and into femur 10 should the surgeon wish to secure foot component 50 in place at the distal femur.

Once the femoral sizing guide 30 is seated in place at the distal femur, as seen in FIG. 3, with the appropriate rotation set between the femoral sizing block 32 and the foot component 50, two options are offered for determining the size of the femoral knee prosthesis to be selected for implant at the implant site 29. In a first sizing option, a reference stylus assembly 80 is coupled with the femoral sizing block 32, as by seating a cylindrical pin 82 of stylus assembly 80 within a complementary cylindrical receptacle 84 in femoral sizing block 32. Stylus assembly 80 includes a reference stylus 86 mounted for sliding movement in angled directions 88 within a post 90. Reference stylus 86 includes a stylus tip 92 which is traced manually across the anterior cortex 94 of the distal femur, in a medial/lateral direction, while the femoral sizing block 32 is held in place upon the distal femur, in the position described above. As the stylus tip 92 follows the contour of the anterior cortex 94, an index mark 96 on the post 90 is viewed and generally will be registered with a size designation 100 on a scale 102 extending along the reference stylus 86. Observation of the index mark 96 enables the surgeon to determine the appropriate size of the femoral knee prosthesis to be implanted.

In a second sizing option, laterally opposite slots 110 are provided in the femoral sizing block 32 in matching pairs corresponding to each available size. With the femoral sizing block 32 in place, as described above, a reference blade 112 is inserted into the slot 110 which enables the reference blade 112 to intersect the anterior cortex 94 for optimum anterior fit. The size designation then is read directly at the corresponding slot 110. Once the size is determined, holes 28 are drilled in the distal femur, employing the pair of drill guides 40 corresponding to the size of the femoral knee prosthesis selected for implant at the implant site 29, thereby assuring the appropriate subsequent location and rotational orientation of the femoral cutting guide on the distal femur.

Figure 4:
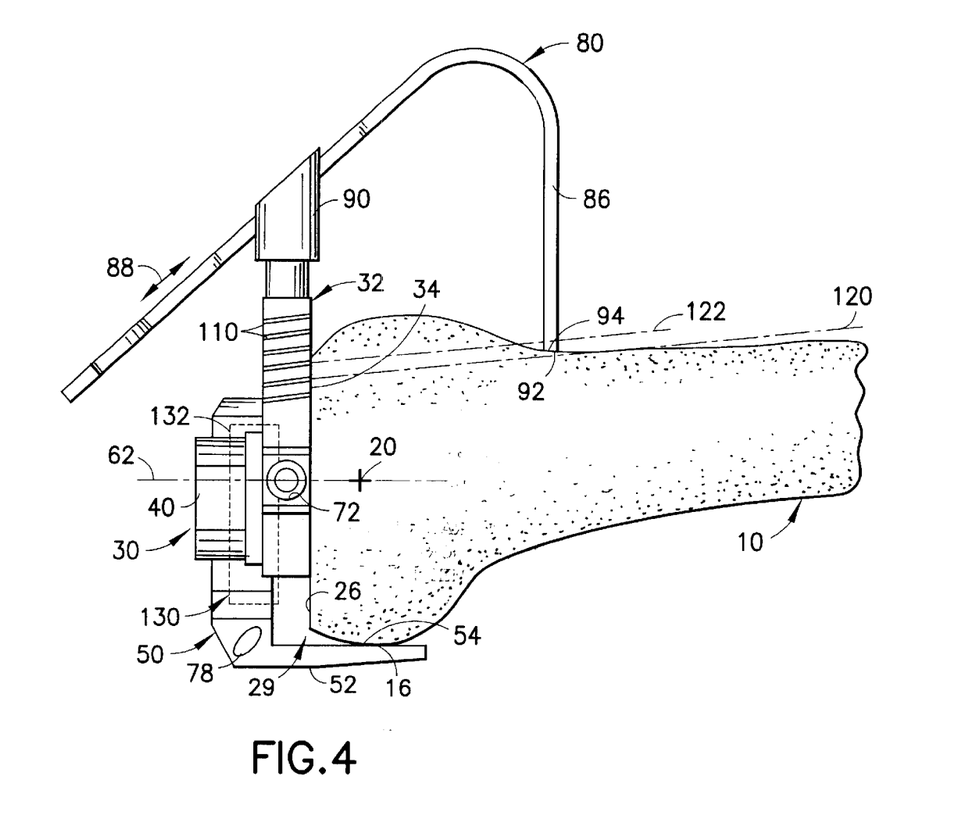
FIG. 4 is a side elevational view of the femoral sizing guide placed at the distal femur and demonstrating another mode of use.

Quite often, the actual sizing indication encountered at a particular implant site will differ from a sizing indication associated with a femoral knee prosthesis of standard size, the actual indicated size usually falling between available standard sizes. In such instances, it becomes necessary for the surgeon to select a femoral knee prothesis of a standard size which is either larger or smaller than the actual indicated size. Thus, as illustrated in FIG. 4, the stylus tip 92 rests against the anterior cortex 94 at an anterior/posterior location which falls between two standard sizes of a femoral knee prosthesis. Preparation of the distal femur for the smaller size would place the plane of the anterior cut at 120, leading to a resection which is too deep, with a potential deleterious notching of the femur 10. Preparation of the distal femur for the larger size would place the plane of the anterior cut at 122, avoiding notching of the femur but leading to a resection which is too proud, with the possible deleterious overstuffing of the patella.

Femoral sizing guide 30 allows avoidance of both of the above-outlined deleterious consequences by enabling the surgeon to adjust the overall position of the drilled holes 28 for an optimum anterior cut. A further connection at 130 connects the foot component 50 with the femoral sizing block 32 for selective anterior and posterior linear movements of the femoral sizing block 32 relative to the foot component 50 and, consequently, relative to feet 52 and the foot locator surfaces 54, through displacements which will compensate for a difference between an actual sizing indication encountered at the implant site 29 and a sizing indication required for the selected femoral knee prosthesis of standard size. Thus, the further connection 130 includes a sliding mechanism, illustrated diagrammatically at 132, for enabling the femoral sizing block 32 to slide in anterior and posterior directions relative to the foot component 50, preferably in predetermined, fixed increments of linear displacement, with the locking knob 68 serving to selectively lock or release the sliding mechanism 132 to either prevent or permit relative linear movement between the femoral sizing block 32 and the foot component 50. As best seen in FIG. 2, an indicator arrangement is shown in the form of an index mark 134 on the femoral sizing block 32 and a scale 136 on the foot component 50 and indicates the increments of relative linear displacement.

Where the actual indicated size for a femoral knee prosthesis falls between two available standard sizes, the surgeon may choose the smaller of the two standard sizes and then compensate by moving the femoral sizing block 32 in a posterior direction relative to the foot component 50, thereby raising the plane of the anterior cut and avoiding notching of the anterior cortex. In the illustrated embodiment, the index mark 134 is moved upwardly from the "0" position to the "−2" position, thereby shifting the position of the holes 28 a distance of 2 mm in the anterior direction, which is lower than the position of the holes 28 necessary for the next larger size. The result is a reduction in the amount of anterior bone removed. Should the surgeon choose the larger of the two available standard sizes the index mark 134 is moved downwardly from the "0" position to the "+2" position, thereby shifting the position of the holes 28 a distance of 2 mm in the posterior direction, which is higher than the position of the holes 28 necessary for the next larger size. The result is a reduction in the amount of posterior bone removed. In this manner, femoral sizing guide 30 better accommodates the range of actual sizes encountered at implant sites in different recipients.

Referring again to FIGS. 2 and 3, femoral sizing block 32 provides a visible indication of the location of the medial and lateral boundaries of a subsequently implanted selected femoral knee prosthesis so as to enable a better interoperative evaluation of fit. To that end, femoral sizing block 32 includes a visual indicator, shown in the form of medial and lateral edges 140 spaced apart laterally a distance corresponding in lateral width to the transverse width of a femoral knee prosthesis of each size. For example, laterally spaced apart edges 140-9 of the femoral sizing block 32 are labelled "9" and, upon seating of the femoral sizing block 32 on the distal femur, serve to indicate visually the location of the lateral boundaries of a selected size "9" femoral knee prosthesis.

Figure 5:
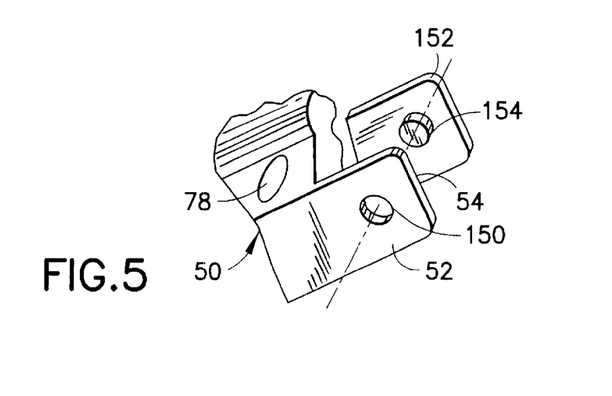
FIG. 5 is a fragmentary bottom and side pictorial perspective view of a portion of the femoral sizing guide.

It will be appreciated that the accuracy with which the holes 28 are located determines the accuracy of the placement of the femoral cutting guide at the distal femur and, consequently, the accuracy of the location of the femoral knee prosthesis being implanted. Since femoral sizing guide 30 is of the type described above, in which the posterior condylar surfaces 16 are employed as reference surfaces, the presence of certain conditions at the posterior condylar surfaces 16, such as those outlined in the aforementioned U.S. Pat. No. 5,810,831, can affect the seating of the femoral sizing guide 30 on the distal femur and the accuracy with which holes 28 are located. These conditions may not necessarily be detected until actually observed by the surgeon during the implant procedure. Hence, femoral sizing guide 30 is constructed so as to enable the surgeon to compensate for any such conditions interoperatively. Accordingly, referring now to FIG. 5, each locator foot 52 includes an aperture 150 which serves as a connection point for shims of different anterior/posterior thicknesses for selective connection to adjust the anterior/posterior position of the locator surfaces 54 relative to the posterior condylar surfaces 16 and thereby compensate for conditions at the posterior condylar surfaces 16 encountered during the implant procedure. One shim is shown at 152 and is seen to have a depending pin 154 for reception within aperture 150 to enable selective location and securement of shim 152 at locator surface 54.

It will be seen that the present invention attains the several objects and advantages summarized above, namely: Provides a single instrument for assisting a surgeon in the interoperative selection of a femoral knee prosthesis of standard size, and fitting the selected component for optimum position and orientation utilizing as a reference the demonstrated reliability of the transepicondylar axis; enables the surgeon to select and fit a femoral knee component of standard size at an implant site where the indicated size requirement does not coincide directly with a standard size, while still attaining optimum positioning and orientation of the implanted femoral knee prosthesis; enables an accurate and stable preparation for the appropriate size femoral knee prosthesis when the sizing procedure initially indicates a size which falls in-between standard available sizes; provides increased accuracy and stability in the location of a femoral guide at the distal femur; lessens the risk of creating an undesirable preparation at the distal femur; provides the surgeon with an advantageous technique for increasing the accuracy of the sizing procedure and concomitant accurate location of an appropriate femoral cutting guide, with added ease and lessened time; minimizes the need for guessing or for visual estimation in determining proper sizing and proper positioning of a femoral cutting guide, and especially proper rotational positioning, during femoral preparations for the implant of a femoral knee prosthesis; permits the surgeon to create a predictable and accurate femoral resection for exemplary performance in the completed implanted knee prosthesis.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. A femoral sizing guide for use in selecting a femoral knee prosthesis of a standard size for implant at an implant site at a distal femur of a femur extending in an axial direction within a recipient, the distal femur having posterior condyles with corresponding posterior condylar surfaces, a prepared distal femoral surface, and a transepicondylar axis extending transverse to the axial direction, the femoral sizing guide being arranged for engagement with the prepared distal femoral surface and the posterior condylar surfaces to provide a size indication for a femoral knee prosthesis of a size appropriate for the implant site, and enabling interoperative determination of an optimum location and orientation of an anterior cut appropriate to accommodate the selected knee prosthesis of standard size at the implant site, the femoral sizing guide comprising:

a femoral sizing block having a block locator surface for extending transverse to the axial direction upon engagement of the femoral sizing block with the prepared distal surface, and a guide arrangement for determining the location of a femoral cutting guide to be placed subsequently at the distal femur for guiding execution of the anterior cut;

a foot component including foot locator surfaces projecting in the axial direction for engaging the posterior condylar surfaces upon engagement of the block locator surface with the prepared distal femoral surface; and a pivotal connection connecting the foot component with the femoral sizing block, the pivotal connection being located for pivotal movement of the femoral sizing block relative to the foot locator surfaces about a pivotal axis extending generally in the axial direction and essentially intersecting the transepicondylar axis so as to enable orientation of the femoral sizing block to locate the guide arrangement for subsequent placement of the femoral cutting guide in position to locate the anterior cut in a plane anterior of and essentially parallel to the transepicondylar axis.

2. The femoral sizing guide of claim 1 wherein the pivotal connection includes an incremental arrangement allowing selective pivotal movement of the femoral sizing block relative to the foot component in predetermined fixed increments of angular displacement.

3. The femoral sizing guide of claim 1 including a further connection connecting the foot component with the femoral sizing block for selective anterior and posterior movements of the femoral sizing block relative to the foot locator surfaces to compensate for any difference between an actual sizing indication encountered at the implant site and a sizing indication required for the selected femoral knee prosthesis of standard size so as to locate the guide arrangement for subsequent placement of the femoral cutting guide in position to enable execution of the anterior cut at a location appropriate to accommodate the selected knee prosthesis of standard size at the implant site.

4. The femoral sizing guide of claim 3 wherein the further connection includes an indicator arrangement allowing selective anterior and posterior movements of the femoral sizing block relative to the foot component in indicated amounts of linear displacement.

5. The femoral sizing guide of claim 3 wherein the selected femoral knee prosthesis of standard size includes medial and lateral boundaries and the femoral sizing block includes a visual indicator corresponding to the medial and lateral boundaries of the selected femoral knee prosthesis such that upon engagement of the block locator surface with the prepared distal femoral surface, the visual indicator provides a visible indication of the subsequent location of the medial and lateral boundaries of the selected femoral knee prosthesis of standard size at the implant site.

6. The femoral sizing guide of claim 5 wherein the selected femoral knee prosthesis of standard size has a transverse width, and the visual indicator includes medial and lateral edges on the femoral sizing block, the medial and lateral edges being spaced apart a transverse distance corresponding to the transverse width of the selected femoral knee prosthesis.

7. The femoral sizing guide of claim 1 wherein the selected femoral knee prosthesis of standard size includes medial and lateral boundaries and the femoral sizing block includes a visual indicator corresponding to the medial and lateral boundaries of the selected femoral knee prosthesis such that upon engagement of the block locator surface with the prepared distal femoral surface, the visual indicator provides a visible indication of the subsequent location of the medial and lateral boundaries of the selected femoral knee prosthesis of standard size at the implant site.

8. The femoral sizing guide of claim 7 wherein the selected femoral knee prosthesis of standard size has a transverse width, and the visual indicator includes medial and lateral edges on the femoral sizing block, the medial and lateral edges being spaced apart a transverse distance corresponding to the transverse width of the selected femoral knee prosthesis.

9. A method of utilizing a femoral sizing guide for implanting a selected femoral knee prosthesis of a standard size at an implant site at a distal femur of a femur extending in an axial direction within a recipient, the distal femur having posterior condyles with corresponding posterior condylar surfaces, a prepared distal femoral surface, and a transepicondylar axis extending transverse to the axial direction, the femoral sizing guide being arranged for engagement with the prepared distal femoral surface and the posterior condylar surfaces to provide a size indication for a femoral knee prosthesis of a size appropriate for the implant site, and enabling interoperative determination of an optimum location and orientation of an anterior cut appropriate to accommodate the selected knee prosthesis of standard size at the implant site, the method comprising:

engaging a femoral sizing block of the femoral sizing guide with the prepared distal surface, the femoral sizing block having a block locator surface such that the block locator surface rests against the prepared distal surface and extends transverse to the axial direction, the femoral sizing block further having a guide arrangement for determining the location of a femoral cutting guide to be placed subsequently at the distal femur for guiding execution of the anterior cut;

engaging a foot component with the posterior condylar surfaces upon engagement of the block locator surface with the prepared distal femoral surface, the foot component including foot locator surfaces projecting in the axial direction for engaging the posterior condylar surfaces; and pivotally moving the femoral sizing block relative to the foot locator surfaces about a pivotal axis extending generally in the axial direction and essentially intersecting the transepicondylar axis so as to enable orientation of the femoral sizing block to locate the guide arrangement for subsequent placement of the femoral cutting guide in position to locate the anterior cut in a plane anterior of and essentially parallel to the transepicondylar axis.

10. The method of claim 9 including moving the femoral sizing block relative to the foot locator surfaces in an anterior/posterior direction to compensate for any difference between an actual sizing indication encountered at the implant site and a sizing indication required for the selected femoral knee prosthesis of standard size so as to locate the guide arrangement for subsequent placement of the femoral cutting guide in position to enable execution of the anterior cut at a location appropriate to accommodate the selected knee prosthesis of standard size at the implant site.

11. The method of claim 10 wherein the selected femoral knee prosthesis of standard size includes medial and lateral boundaries and the method includes providing the femoral sizing block with a visual indicator corresponding to the medial and lateral boundaries of the selected femoral knee prosthesis such that upon engagement of the block locator surface with the prepared distal femoral surface, the visual indicator enables a visible indication of the subsequent location of the medial and lateral boundaries of the selected femoral knee prosthesis of standard size at the implant site.

12. A femoral guide for use in connection with implanting a femoral knee prosthesis at an implant site at a distal femur of a femur extending in an axial direction within a recipient, the distal femur having a transepicondylar axis extending transverse to the axial direction, the femoral guide being arranged for engagement with the distal femur to enable interoperative determination of an optimum location and orientation of at least one femoral cut appropriate to accommodate the knee prosthesis at the implant site, the femoral guide comprising:

a femoral block for engagement with the distal femur, the femoral block having a guide arrangement for determining the location and orientation of the at least one femoral cut;

a support component for placement at a predetermined position relative to the distal femur; and a pivotal connection connecting the support component with the femoral block, the pivotal connection being located for pivotal movement of the femoral block relative to the support component about a pivotal axis extending generally in the axial direction and essentially intersecting the transepicondylar axis so as to enable orientation of the femoral block to rotationally position the guide arrangement for subsequent rotational orientation of the at least one femoral cut relative to the transepicondylar axis.

13. The femoral guide of claim 12 wherein the support component includes support elements for engaging the distal femur to locate the support component at the predetermined position.

14. The femoral guide of claim 13 wherein the guide arrangement includes guide elements for determining the location of a femoral cutting guide to be placed subsequently at the distal femur for guiding execution of the at least one femoral cut.

15. The femoral guide of claim 12 wherein the pivotal connection includes an incremental arrangement allowing selective pivotal movement of the femoral block relative to the support component in predetermined fixed increments of angular displacement.

16. The femoral guide of claim 12 including a further connection connecting the support component with the femoral block for selective anterior and posterior movements of the femoral block relative to the support block.

17. The femoral guide of claim 16 wherein the further connection includes an indicator arrangement allowing selective anterior and posterior movements of the femoral block relative to the support component in indicated amounts of linear displacement.

18. The femoral guide of claim 16 wherein the femoral knee prosthesis includes medial and lateral boundaries and the femoral block includes a visual indicator corresponding to the medial and lateral boundaries of the femoral knee prosthesis such that upon engagement of the femoral block with the distal femur, the visual indicator provides a visible indication of the subsequent location of the medial and lateral boundaries of the femoral knee prosthesis at the implant site.

19. The femoral guide of claim 18 wherein the femoral knee prosthesis has a transverse width, and the visual indicator includes medial and lateral edges on the femoral block, the medial and lateral edges being spaced apart a transverse distance corresponding to the transverse width of the femoral knee prosthesis.

20. The femoral guide of claim 12 wherein the femoral knee prosthesis includes medial and lateral boundaries and the femoral block includes a visual indicator corresponding to the medial and lateral boundaries of the femoral knee prosthesis such that upon engagement of the femoral block with the distal femur, the visual indicator provides a visible indication of the subsequent location of the medial and lateral boundaries of the femoral knee prosthesis at the implant site.

21. The femoral guide of claim 20 wherein the femoral knee prosthesis has a transverse width, and the visual indicator includes medial and lateral edges on the femoral block, the medial and lateral edges being spaced apart a transverse distance corresponding to the transverse width of the femoral knee prosthesis.

22. A method of utilizing a femoral guide in connection with implanting a femoral knee prosthesis at an implant site at a distal femur of a femur extending in an axial direction within a recipient, the distal femur having a transepicondylar axis extending transverse to the axial direction, the femoral guide being arranged for engagement with the distal femur to enable interoperative determination of an optimum location and orientation of at least one femoral cut appropriate to accommodate the knee prosthesis at the implant site, the method comprising:

engaging a femoral block of the femoral guide with the distal femur, the femoral block further having a guide arrangement for determining the location and orientation of the at least one femoral cut;

placing a support component at a predetermined position relative to the distal femur; and pivotally moving the femoral block relative to the support component about a pivotal axis extending generally in the axial direction and essentially intersecting the transepicondylar axis so as to enable orientation of the femoral block to rotationally position the guide arrangement for subsequent rotational orientation of the at least one femoral cut relative to the transepicondylar axis.

23. The method of claim 22 wherein placing the support component at the predetermined position includes engaging support elements of the support component with the distal femur to locate the support component at the predetermined position.

24. The method of claim 23 wherein pivotally moving the femoral block relative to the support block includes determining the location of a femoral cutting guide to be placed subsequently at the distal femur for guiding execution of the at least one femoral cut.

25. The method of claim 22 including moving the femoral block relative to the foot locator surfaces in an anterior/posterior direction to compensate for any difference between an actual sizing indication encountered at the implant site and a sizing indication required for the femoral knee prosthesis so as to locate the guide arrangement for enabling execution of the at least one femoral cut at a location appropriate to accommodate the knee prosthesis at the implant site.

26. The method of claim 25 wherein the femoral knee prosthesis includes medial and lateral boundaries and the method includes providing the femoral block with a visual indicator corresponding to the medial and lateral boundaries of the femoral knee prosthesis such that upon engagement of the femoral block at the distal femur, the visual indicator enables a visible indication of the subsequent location of the medial and lateral boundaries of the femoral knee prosthesis at the implant site.

* * * * *